(12) United States Patent
Tavassoli et al.

(10) Patent No.: US 7,405,304 B2
(45) Date of Patent: Jul. 29, 2008

(54) METHODS FOR THE PREPARATION OF ALKYL DIARYL BORINATES AND COMPLEXED DIARYLBORONIC ACIDS

(75) Inventors: Ali Tavassoli, State College, PA (US); Stephen J. Benkovic, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 373 days.

(21) Appl. No.: 10/501,755

(22) PCT Filed: Jan. 9, 2003

(86) PCT No.: PCT/US03/00768

§ 371 (c)(1),
(2), (4) Date: Nov. 12, 2004

(87) PCT Pub. No.: WO03/059916

PCT Pub. Date: Jul. 24, 2003

(65) Prior Publication Data

US 2005/0080048 A1    Apr. 14, 2005

Related U.S. Application Data

(60) Provisional application No. 60/347,811, filed on Jan. 10, 2002.

(51) Int. Cl.
*C07D 231/00* (2006.01)
(52) U.S. Cl. .......................................... 548/110; 514/64
(58) Field of Classification Search ................. 548/110; 514/64
See application file for complete search history.

(56) References Cited

U.S. PATENT DOCUMENTS

| | | | |
|---|---|---|---|
| 3,485,864 | A | 12/1969 | Birnbaum et al. |
| 4,199,574 | A | 4/1980 | Schaeffer |
| 4,713,346 | A | 12/1987 | Gallop et al. |
| 5,130,302 | A | 7/1992 | Spielvogel et al. |
| 5,348,947 | A | 9/1994 | Patel |
| 5,348,948 | A | 9/1994 | Patel |
| 5,362,732 | A | 11/1994 | Spielvogel et al. |
| 5,789,416 | A | 8/1998 | Lum et al. |
| 6,287,713 | B1 | 9/2001 | Heuer et al. |
| 6,420,301 | B1 | 7/2002 | Kristen et al. |
| 6,734,457 | B2 | 5/2004 | Yamazaki et al. |
| 7,019,055 | B2 | 3/2006 | Wang |

FOREIGN PATENT DOCUMENTS

| | | |
|---|---|---|
| DE | 1 982 640 3 | 12/1999 |
| DE | 198 29 949 | 1/2000 |
| EP | 0 967 220 A1 | 12/1999 |
| EP | 0 969 531 | 1/2000 |
| EP | WO 00/44387 A1 | 8/2000 |
| EP | 1155698 | 11/2001 |
| EP | 1 420 021 A1 | 5/2004 |
| ES | 2185358 | 4/2003 |
| FR | 2 071 171 | 9/1971 |
| JP | 2000-150163 | 5/2000 |
| JP | 2001 342192 A2 | 12/2001 |
| JP | 2002-518404 | 6/2002 |
| JP | 2002 322007 A2 | 11/2002 |
| JP | 2003-501431 | 1/2003 |
| JP | 2003-229275 | 8/2003 |
| KR | 2000-011462 | 2/2000 |
| TW | 419928 B | 1/2001 |
| WO | WO 98/08855 | 3/1998 |
| WO | WO 98/12206 | 3/1998 |
| WO | WO 99/65923 | 12/1999 |
| WO | WO 00/56812 A1 | 9/2000 |
| WO | WO 00/75142 A2 | 12/2000 |
| WO | WO 02/44184 A3 | 6/2002 |
| WO | WO 03/033002 A1 | 4/2003 |
| WO | WO03/059916 A2 | 7/2003 |
| WO | WO 2004/056322 A3 | 9/2004 |

OTHER PUBLICATIONS

Yuan et al., 1989, CAS: 112:139083.*
Imazaki et al., 2000, CAS: 133:144898.*
Torres et al., 1994, CAS: 120:332485.*
Liu et al., 1991, CAS: 115:219486.*
Yuan et al., 1998, CAS: 109:54817.*
Yu et al., 1991, CAS 114:143497.*
Rettig et al., 1974, CAS: 81:128040.*
Alberti, A. et al., "Reactions of Triphenylborane with Photoexcited Ketones and with Diazodiarylmethanes," *Journal of Organometallic Chemistry*, 1985, 297:13-19.
Anderson, S. et al., "Materials for organic electroluminescence: aluminum vs. boron," *Synthetic Metals*, 2000, 111-112:459-463.
Campbell, N. et al., "Tautomerism in the Solid State. Part II.," *J. Chem. Soc.*, Mar. 1961, 1191-1194.
Dorokhov, V.A. et al., "Boron chelate complexes with some enamiones and diketones containing pyridine moiety and their mutual transformation in solutions," *Izvestiya Akademii Nauk*, Seriya Khimicheskaya, 1996, 3:710-714.
Farfán, N. et al., "Through-bond Modulation of N→B Ring Formation shown by NMR and X-Ray Diffraction Studies of Borate Derivatives of Pyridyl Alcohols," *J. Chem. Soc. Perkin Trans 2*, 1992, 4:527-532.
Florencio, F. et al., "The crystal structure of [bis(α-pyridyl)bis(diphenlboranoxy)]methane," *Zeitschrift fuer Kristallographie*, 1984, 168:173-178.
Friese, B. et al., "Constitution of the 1,5-diphenylcarazonato-diphenylboron chelate—a chemical approach," *Monatshefte fuer Chemie*, 1978, 109(3):711-718.

(Continued)

*Primary Examiner*—Rei-Tsang Shiao
(74) *Attorney, Agent, or Firm*—McDonnell Boehnen Hulbert & Berghoff LLP

(57) ABSTRACT

The present invention provides methods for preparing complexed diaryl boronic acids from alkyl diarylborinates.

4 Claims, No Drawings

OTHER PUBLICATIONS

Hawthorne, M. et al., "Amine Boranes. I. The Preparation of Pyridine Arylboranes", *J. Amer. Chem. Soc.*, 1958, 80:4291-4296.

Hawthorne, M. et al., "Amine Boranes. II. The Preparation of Pyridine Diarylboranes", *J. Amer. Chem. Soc.*, 1958, 80:4291-4296.

Haynes, R.R. et al., "Aryl Boronic Acids. VIII. Reactions of boronophthalide," *Journal of Organic Chemistry*, Nov. 1964, 29(11):3229-3233.

Hohaus, E. et al., "Boron chelates and boron metal chelates. I. Boron chelates with chelating agents of they pyridine and quinoline series and their N-oxides," *Chemische Berichte*, 1969, 102(12):4025-4031.

Hohaus, E. et al., "Mass spectrometric studies of boron chelates of the pyridine and quinoline series and their N-oxides," *Zeitschrift fuer Naturforschung, Teil B: Anorganische Chemie, Organische Chemie, Biochemie, Biophysik, Biologie*, Jul./Aug. 1973, 28(7-8):440-445.

Hohaus, E. et al., "Mass spectrometric investigation of boron chelates, III. Mass spectrometric fragmentation of fluoroboron and phenylboron chelates," *Zeitschrift fuer Naturforschung, Teil B: Anorganische Chemie*, Organische Chemie, Mar. 1976, 31B(3):324-329.

Höpfl, H. et al., "X-Ray Crystallographic Study of Three (N→B)-Borinates Prepared From 8-Hydroxyquinoline and 2-Hydroxypyridine," *Chemistry of Heterocyclic Compounds*, 1999, 35(8):912-927.

Kliegel, W. et al., "Molecular rearrangement of cyclic boron-nitrogen betaines," *Materials Science Monographs*, 1985, 28B (React. Solids, Pt. B): 725-726.

Lin, K. et al., "Synthesis and antitumor activity of organyloxy-diarylborane chelates containing quinoline ring," *Yiyao Gongye (Pharmaceutical Industry)*, 1985, 16(11):500-502.

Liu, X. et al., "Structure studies of bis(substituted)-2-(substituted)-8-hydroxyquinolines," *Youji Huaxue (Chinese Journal of Organic Chemistry)*, Aug. 1991, 11(4):410-415.

Michailow, W. et al., *Izv. Akad. Nauk SSSR SER.KHIM*, 1956, 451-453.

Moehrle, H. et al., "Conformation influences during the dehydrogenation of phenolic Mannich bases," *Monatshefte fuer Chemie*, 1974, 105(6):1151-1163.

Moehrle, H. et al., "Real structures of drugs seemingly derived from 1-(8-hydroxyquinol-5-yl)-3-phenylpropane-1,3-dione," *Pharmazie*, 1985, 40(5):307-311.

Moehrle, H. et al., "Reaction of functional epoxycarbonyl compounds opposed to hydrogen chloride," *Pharmazie*, 1985, 40(6):387-393.

Moehrle, H. et al., "Concurrent reaction of the phenol and the 1,3-dicarbonyl function under Mannich conditions," *Pharmazie*, 1985, 40(11):767-771.

Morozova, T.L. et al., "Thermal decomposition of organoaluminum and organoboron compounds with intramolecular coordination," *Term. Anal. Fazovye Ravnovesiya*, 1985, 31-33, Publisher: Permsk. Gos. Univ., Perm, USSR.

Neu , R., "The identification of boron in organic bondings," *Z. Anal. Chem.*, 1960, 176(5):343-346.

Neu, R., "Coordination compounds from diphenylboric acid and substances with ring nitrogen as the electron donors," *Chemical Abstracts*, 1961, 10G—Heterocyclic Compounds:14457.

Parts, L. et al., "Oxidation of Methylboranes at 77—170α K.," *Inorg. Chem.*, Nov. 1964, 3(11):1483-1486.

Peyton, J. et al., *J. Organomet. Chem.*, 1978, 156:101-110.

Roth, H. et al., "Specificity of the TTC reaction. VI. Mechanism of the TTC reaction of pyridinium carbinols. Reaction of N-methylpyridinium-2-carbinol hydroxide wth triphenylboron," *Archiv der Pharmazie und Berichte der Deutschen Pharmazeutischen Gesellschaft*, 1967, 300(1):44-52.

Shan, Z. et al., "Syntheses of aromatic nitrogen-containing heterocyclic derivatives of asymmetric diarylborinic acids," *Wuhan Daxue Xuebao, Ziran Kexueban (Journal of Wuhan University, Natural Science Edition )*, 1990, 3:67-72.

Tabuchi, H. et al., "Synthesis and Anticoccidial Activity of Some Azacyclo Organoborniates," *Heterocycles*, 2002, 57(7):1319-1326.

Tabuchi, H. et al., "Anticoccidial Activity of Some Azacyclo Organoborinates," i Heterocycles, 2003, 60(1):177-182.

Thierig, D. et al., "Photometric determination of diphenylborinic acid and its esters with diphenylcarbazone," *Zeitschrift fuer Analytische Chemie*, 1966, 215(1):24-30.

Titkov, Y.B., "Luminescence method for determining molybdenum with hydroxyquinoline and sodium tetraphenylborate," *Ukrainskii Khimicheskii Zhurnal (Russian Edition)*, 1970, 36(6):613-615.

Torres, L. et al., "Rotating-bomb combustion calorimetry and the standard enthalpies of formation of two borinic esters," *J. Chem. Thermodynamics*, 1994, 26:337-343.

Trujillo, J. et al., "X-ray crystallographic study of boroxazolidones obtained from L-ornithine, L-methionine, kainic acid and 2,6-pyridinedicarboxylic acid," *Journal of Organometallic Chemistry*, 1998, 571:21-29.

Wu, Q. et al., Synthesis, Structure, and Electroluminescence of $BR_2q$ (R = Et, Ph, 2-Naphthyl and q = 8-Hydroxyquinolato), *Chem. Mater.*, 2000, 12:79-83.

Yu, D. et al., "Proton and boron-11 NMR spectroscopy of diarylboron chelates containing boron-nitrogen coordinate bonds and of triboranes," *Fenxi Ceshi Tongbao*, 1990, 9(4):5-10.

Yuan, G. et al., "Studies on antitumor boron compounds. V. Fluorine- and methoxy-substituted diphenylboron chelates with N, O-bidentate ligands," *Youji Huaxue (Chinese Journal of Organic Chemistry)*, Jun. 1989, 9(3):226-229.

Yuan, G. et al., "Ligand substitution reaction of diarylboron chelates," *Wuji Huaxue Xuebao (Journal of Inorganic Chemistry)*, Sep. 1990, 6(3):314-318.

Yuan, G. et al., "Single site transarylation of 2,2'-dimetalized 1,1'-binaphthyl to aminochloroborates and synthesis of 2-binaphthyl boron compounds," *Youji Huaxue (Chinese Journal of Organic Chemistry*, Apr. 1996, 16(2):139-144.

Zhang, G. et al., *Youji Huaxue (Chinese Journal of Organic Chemistry)*, 1982, 6:409-412.

Zimmerman, H.K., "Diphenylboron Esters of 2-pyridylalkanol Derivatives," *Texas J. Sci.*, Jun. 1963, 15(2):192-199.

Heitman, J., "On the Orgins, Structures and Function of Restriction-Modification Enzymes", *Genetic Engineering*, 1993, 15:57-108.

May, M. et al., "Analysis of Bacteriophage Deoxyribonucleic Acid Sequences Methylated by Host- and R-Factor-Controlled Enzymes", *Journal of Bacteriology*, Aug. 1975, 123(2):768-770.

Marinus, M. et al., "Isolation of Deoxyribonucleic Acid Methylase Mutants of *Escherichia coli* K-12", *Journal of Bacteriology*, Jun. 1973, 114(3):1143-1150.

Palmer, B. et al., "The *dam* and *dcm* Strains of *Escherichia coli*—a Review", Gene, 143:1-12.

Kuhnz, W. et al., "Predicting the Oral Bioavailability of 19-Nortestosterone Progestins In Vivo From Their Metabolic Stability In Human Liver Microsomal Preparations In Vitro", *Drug Metabolism and Disposition*, 1998, 26(11):1120-1127.

Jost, J. et al., "The Formulation of DNA Methylation Patterns and the Silencing of Genes", *Progress in Nucleic Acid Research and Molecular Biology*, 1997, 57:217-248.

Berdis, A. et al., "A Cell Cycle-Regulated Adenine DNA Methyltransferase From *Caulobacter crescentus* Processively Methylates GANTC Sites on Hemimethylated DNA", *Proc. Natl. Acad. Sci. USA*, Mar. 1998, 95:2874-2879.

Thierig, D.; Umland F., "Photometric determination of diphenylborinic acid and its esters with dipehnylcarbazone", *Chemical Abstracts*, vol. 64, 1966, 11863-11864.

Beilstein Institut zur Forderung der Chemischen Wissenschaftern, Database accession No. 759640, XP002239683 abstract, *J. Amer. Chem. Soc.*, vol. 80, 1958, p. 4291.

Beilstein Institut zur Forderung der Chemischen Wissenschaftern, Database accession No. 762485, XP002239684 abstract, Izv. Akad. Nauk Sssr Ser. Khim, 1956, pp. 451-453.

Haynes, et al., "Arylboronic Acids—(VIII) reactions of boronophthalide", Chemical Abstract, vol. 61, pp. 16083-16084.

* cited by examiner

METHODS FOR THE PREPARATION OF ALKYL DIARYL BORINATES AND COMPLEXED DIARYLBORONIC ACIDS

CROSS-REFERENCE TO RELATED APPLICATIONS

This application claims priority from U.S. Provisional Application Ser. No. 60/347,811, filed Jan. 9, 2002, the disclosure of which is incorporated herein by reference in its entirety.

BACKGROUND OF THE INVENTION

1. Field of the Invention

This invention relates to methods for preparing alkyl diarylborinates and methods for preparing complexed diarylboronic acids, which are useful as antibacterial agents.

2. Description of the Related Art

N—O complexed diarylboronic acids are known to be effective pharmaceutical agents. For example, such compounds are capable of inhibiting adenine DNA methyltransferases in bacterial cells and thus exhibit antibacterial, growth-inhibitory properties against any bacterial species that produces an adenine DNA methyltransferase. Antibacterial diarylboronic acids are described in International Application Publication No. WO 00/75142.

Currently available methods for the preparation of N—O complexed diarylboronic acids require the use of dichloroborane methyl sulfide complex as a starting material. The use of dichloroborane methyl sulfide complex has several disadvantages, including the formation of dimethyl sulfide (DMS) as a side product of the reaction. Further, dichloroborane methyl sulfide reacts violently with water to produce flammable and harmful gases and has a repugnant odor that causes great discomfort for any lab personnel working with the material.

The formation of DMS as a side product makes the process of isolating a reaction product without contaminating the working area with DMS extremely difficult. Like dichloroborane methyl sulfide complex, DMS also has a foul odor. Further, DMS is a cancer suspect agent.

A need exists, therefore, for a method for preparing N—O complexed diarylboronic acids, and complexed diarylboronic acids in general, that is safer, more versatile and friendlier to lab personnel than currently known methods.

SUMMARY OF THE INVENTION

The present invention provides a method for preparing a compound of the formula I:

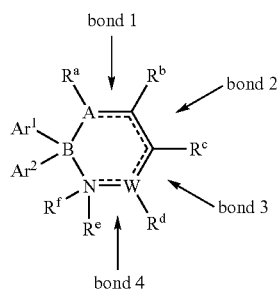
(I)

The invention also provides a method for preparing a compound of formula III:

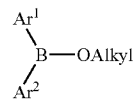
(III)

The invention further provides compounds of formula I and formula III prepared according to the methods of the invention.

The methods of the invention are advantageous, inter alia, because they permit efficient synthesis of alkyl diarylborinates using reagents that are less toxic, less noxious and less dangerous than conventional reagents used in these syntheses.

Specific preferred embodiments of the present invention will become evident from the following more detailed description of certain preferred embodiments and the claims.

DETAILED DESCRIPTION OF THE PREFERRED EMBODIMENT

As indicated above, the invention provides methods of preparing compounds of formula I:

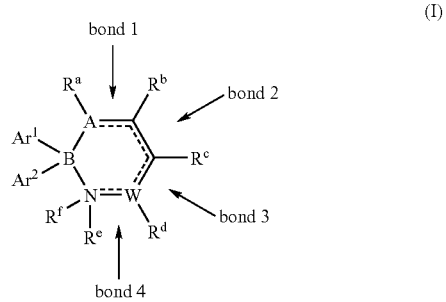
(I)

wherein A is N, O or S;

W is $C_p$, where p is 0 or 1;

$R^a$, $R^b$, $R^c$, $R^d$, and $R^e$ are the same or different and are independently hydrogen, halogen, nitro, nitroso, lower alkyl, aryl or substituted aryl, lower alkoxy, lower alkoxyalkyl, or cycloalkyl or cycloalkyl alkoxy, where each cycloalkyl group has from 3-7 members, where up to two of the cycloalkyl members are optionally hetero atoms selected from sulfur, oxygen and nitrogen, and where any member of the alkyl, aryl or cycloalkyl group is optionally substituted with halogen, lower alkyl or lower alkoxy, aryl or substituted aryl, halogen, nitro, nitroso, aldehyde, carboxylic acid, amide, ester, or sulfate, or wherein $R^a$, $R^b$, $R^c$, $R^d$, and $R^e$ may be connected by aromatic, aliphatic, heteroaromatic, heteroaliphatic ring structures or substituted embodiments thereof, where $R^a$ is absent when A is O or S and $R^d$ is absent when p=0;

$R^f$ is hydrogen or is absent; and wherein $Ar^1$ and $Ar^2$ can be the same or different and are each independently thienyl, aryl or aryl substituted at one or a plurality of positions with halogen, nitro, nitroso, lower alkyl, aryl or substituted aryl, lower alkoxy, lower alkoxyalkyl, or cycloalkyl or cycloalkyl alkoxy, where each cycloalkyl group has from 3-7 members, where up to two of the cycloalkyl members are optionally hetero atoms selected from sulfur, oxygen and nitrogen, and where any member of the alkyl, aryl or cycloalkyl group is optionally substituted with halogen, lower alkyl or lower alkoxy, aryl or substituted aryl, halogen, nitro, nitroso, aldehyde, carboxylic acid, amide, ester, or sulfate, and wherein bond 1, bond 2, bond 3 and bond 4 are independently a single bond or a double bond, provided that when A is S or O, bond 1 is a single bond and where A is N, bond 1 is a double bond.

Compounds of formula I are useful as pharmaceutical agents. For example, compounds of formula I are antibacterial compounds, as described in International Application Publication No. WO 00/75142, and pending U.S. patent application Ser. No. 09/578,991, filed May 25, 2000, each of which is incorporated herein by reference in its entirety.

The methods of the invention for preparing compounds of formula I are depicted in Reaction Schemes 1 and 2.

REACTION SCHEME 1

$Ar^1M \ + \ Ar^2M \ + \ B(O\text{—}alkyl)_3$

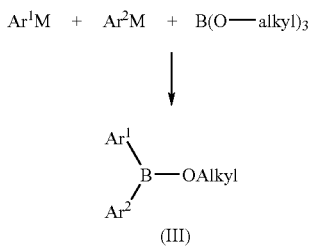

(III)

M is, for example, MgBr or Li

REACTION SCHEME 2

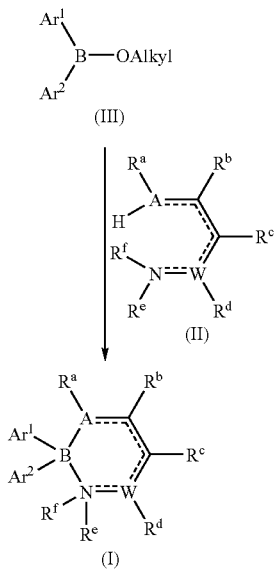

Referring to Reaction Scheme 1, a trialkylborate is reacted with metalloorganic reagents $Ar^1M$ and $Ar^2M$ to form an alkyl diarylborinate of formula III. Preferably, the reaction is conducted by the addition of the trialkylborate to the metalloorganic reagents in an aprotic, non-aqueous solvent, such as tetrahydrofuran (THF) or diethyl ether. Also preferably, the addition is conducted under an inert atmosphere, such as a nitrogen or noble gas atmosphere, and at a temperature lower than room temperature, more preferably a temperature lower than 0° C. For example, the addition is advantageously conducted at −78° C. under argon gas.

Following completion, the reaction is worked up by either a non-acidic workup step or by an acidic workup step. A non-acidic workup is preferred. In a non-acidic workup, the reaction mixture is treated with an excess of an organic solvent, most preferably an alcohol solvent such as methanol. The product is then isolated from the reaction mixture by known methods, such as by removal of the solvent under vacuum, and then the alkyl boronate is extracted with an ether or other organic solvent from the aqueous metal salts from the metalloorganic reagent. In the less preferred acidic workup step, an acidic solvent, such as dilute hydrochloric acid, is added to the reaction mixture to give a diaryl boronic acid ($Ar^1Ar^2B$—OH). The boronic acid is then converted to the borinate of formula III by treating the boronic acid with an alcohol such as methanol.

Metalloorganic reagents suitable for use in the methods of the invention include Grignard reagents and organic alkali metal compounds, wherein the alkali metal is lithium or sodium. Other metalloorganic reagents are known in the art, such as zinc, copper and lithium metalloorganic reagents, can be used. A preferred metalloorganic reagent is a Grignard reagent. Grignard reagents are well known, and many are commercially available. Others can be readily prepared by known methods. At least two equivalents of metalloorganic reagent are used for each equivalent of alkylborate. A single metalloorganic reagent can be used (i.e., where $Ar^1M$ and $Ar^2M$ in Scheme 1 are the same), thus yielding an alkyl diarylborinate $Ar^1Ar^2B$—O-alkyl in which $Ar^1$ and $Ar^2$ are the same. Alternatively, two different metalloorganic reagents can be used, yielding an alkyl diarylborinate in which $Ar^1$ and $Ar^2$ are not the same.

Any alkylborate, $B(O\text{-Alkyl})_3$, is suitable for use in the reaction described above. Preferred alkylborates include lower alkyl boronates, comprising 1-6 carbon atoms per alkyl group. Examples of preferred alkylboronates include but are not limited to trimethylborate, triethylborate, tributylborate or mixtures thereof. A more preferred alkylborate is trimethylborate. Alkylborates are commercially available (for example from Sigma-Aldrich, Milwaukee, Wis.) or can be readily prepared by known methods.

Referring to Reaction Scheme 2, the alkyl diarylborinate of formula III prepared as described in Reaction Scheme 1 is complexed with a complexing agent of formula II. Preferably, the complexing step is performed by dissolving or dispersing the complexing agent of formula II in a solvent and adding the solution or dispersion to a solution or dispersion of the alkyl diarylborinate of formula III. The product compound of formula I can be isolated by a variety of techniques including crystallization and filtration, or removal of solvent in vacuum. The product can be purified by known methods, including recrystallization, and/or chromatograhy.

The complexing agent II can be any compound containing an amino group and either a hydroxy, a thiol or a second amino group. The amino group and the hydroxy, thiol or second amino group are separated by 2 or 3 carbon atoms. Examples of such complexing agents include:

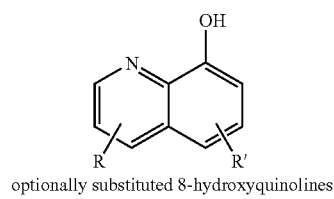

optionally substituted 8-hydroxyquinolines

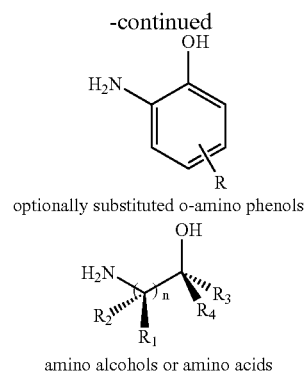

optionally substituted o-amino phenols amino alcohols or amino acids wherein, n is 1 or 2;

R and R' are the same or different and are independently hydrogen, halogen, lower alkyl or lower alkoxy, aryl or substituted aryl, halogen, nitro, nitroso, aldehyde, carboxylic acid, amide, ester, or sulfate, and $R_1$, $R_2$, $R_3$, and $R_4$ are the same or different and are independently hydrogen, halogen, nitro, nitroso, lower alkyl, aryl or substituted aryl, lower alkoxy, lower alkoxyalkyl, or cycloalkyl or cycloalkyl alkoxy, where each cycloalkyl group has from 3-7 members, where up to two of the cycloalkyl members are optionally hetero atoms selected from sulfur, oxygen and nitrogen, and where any member of the alkyl, aryl or cycloalkyl group is optionally substituted with halogen, lower alkyl or lower alkoxy, aryl or substituted aryl, halogen, nitro, nitroso, aldehyde, carboxylic acid, amide, ester, or sulfate, or $R_1$, $R_2$, $R_3$, and $R_4$ may be connected by aromatic, aliphatic, heteroaromatic, heteroaliphatic ring structures or substituted embodiments thereof.

Preferred compounds of Formula I prepared according to the methods of the invention include those wherein A is oxygen.

Preferred compounds of Formula I prepared according to the methods of the invention also include those wherein $Ar^1=Ar^2$.

Preferred compounds of Formula I prepared according to the methods of the invention also include those wherein $Ar^1$ and $Ar^2$ are selected from:

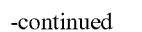
(i)

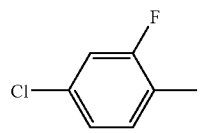
(ii)

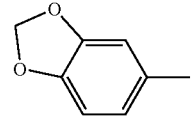
(iii)

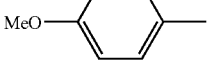
(iv)

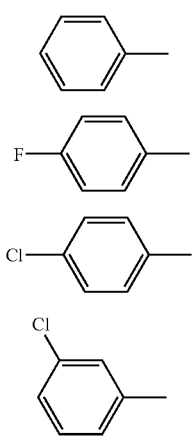

(v)

(vi)

(vii)

(viii)

Preferred compounds of Formula II prepared according to the methods of the invention include:

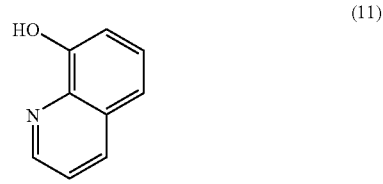
(11)

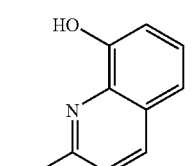
(12)

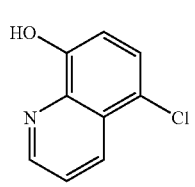
(13)

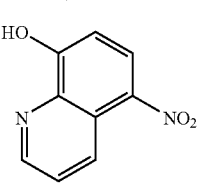
(14)

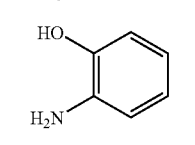
(15)

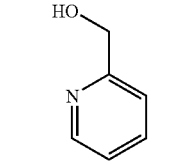
(16)

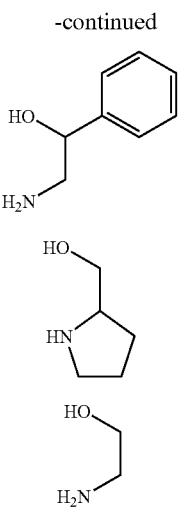

The methods of the invention have several distinct advantages over other procedures for the preparation of complexed diarylboronic acids. For example, by using a trialkylborate as a starting material, chloroborane methyl sulfide is not required and the concomitant formation of DMS as a side product is avoided. As a result, the process of isolating a reaction product is greatly simplified. Additionally, when trialkylborate reacts with water it produces alcohols, which are relatively harmless substances compared with the reaction side products produced according to the prior art.

In an industrial setting where large quantities of reagents are required, trialkylborinates are more appealing starting materials than the previously used reagents, not only because of the inherent safety of the borinates, but also because of their cost. Trimethylborate, for example, is considerably less expensive than previously used reagents.

The presence of an alkyl ester in compounds of formula III allows this compound to form a complex with a wider variety of complexing agents of formula II than was previously possible. This is due in part to increased solubility of the compound of formula III and because there is a decreased possibility of side reactions and side products using these compounds. Previous methods for synthesizing complexed diarylboronic acids used a boronic acid in the complexing step. Boronic acids, however, can react with any amine (base) in the complexing agent to produce a salt, which produces an undesired product. The boronic esters of formula III of the invention, on the other hand, can react with a wider variety of compounds, including compounds containing hydrophilic or polar charged substituents, without producing such undesired products.

A further advantage of the methods of the invention is that diarylborinates of formula III in the invention are prepared in a single step. Prior art methods prepared boronic acid in a first step and required a second step to produce the alkyl boronate, and are thus less robust than the instant methods.

Compounds of Formula I prepared according to the methods of the invention may contain one or more asymmetric carbon atoms, so that the compounds can exist in different stereoisomeric forms. These compounds can be, for example, racemates or optically active forms. In these situations, the single enantiomers, i.e., optically active forms, can be obtained by asymmetric synthesis or by resolution of the racemates. Resolution of the racemates can be accomplished, for example, by conventional methods such as crystallization in the presence of a resolving agent, or chromatography using, for example a chiral HPLC column.

Compounds prepared according to the methods of the invention can exist as tautomers in solution. When structures and names are given for one tautomeric form the other tautomeric form is also included in the invention.

Representative compounds prepared according to the methods of the present invention include, but are not limited to the compounds disclosed herein and their pharmaceutically acceptable acid and base addition salts. In addition, if a compound is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds.

In the description of the reagents and methods of this invention, particular terms are defined as follows.

By "alkyl", "lower alkyl", and "$C_1$-$C_6$ alkyl" in the present invention is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl.

By "alkoxy", "lower alkoxy", and "$C_1$-$C_6$ alkoxy" in the present invention is meant straight or branched chain alkoxy groups having 1-6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy.

By the term "halogen" in the present invention is meant fluorine, bromine, chlorine, and iodine.

By "aliphatic ring" or "cycloalkyl", e.g., $C_3$-$C_7$ cycloalkyl, in the present invention is meant cycloalkyl groups having 3-7 atoms such as, for example cyclopropyl, cyclobutyl, cyclopentyl, cyclohexyl, and cycloheptyl. In the $C_3$-$C_7$ cycloalkyl groups, preferably in the $C_5$-$C_7$ cycloalkyl groups, one or two of the carbon atoms forming the ring can optionally be replaced with a heteroatom, such as sulfur, oxygen or nitrogen. Examples of such groups are piperidinyl, piperazinyl, morpholinyl, pyrrolidinyl, imidazolidinyl, oxazolidinyl, azaperhydroepinyl, oxazaperhydroepinyl, oxepanyl, oxazaperhydroinyl, and oxadiazaperhydroinyl. $C_3$ and $C_4$ cycloalkyl groups having a member replaced by nitrogen or oxygen include aziridinyl, azetidinyl, oxetanyl, and oxiranyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, lower alkyl, lower alkoxy, lower alkylthio, trifluoromethyl, lower acyloxy, aryl, heteroaryl, and hydroxy. Preferred aryl groups include phenyl and naphthyl, each of which is optionally substituted as defined herein.

By "heteroaromatic" or "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, and benzoxazolyl. Preferred heteroaryls are thiazolyl, pyrimidinyl, preferably pyrimidin-2-yl, and pyridyl. Other preferred heteroaryl groups include 1-imidazolyl, 2-thienyl, 1-, or 2-quinolinyl, 1-, or 2-isoquinolinyl, 1-, or 2-tetrahydro isoquinolinyl, 2- or 3-furanyl and 2-tetrahydrofuranyl.

By "aliphatic ring," or "heterocycle," is meant one or more carbocyclic ring systems of 3-, 4-, 5-, 6-, or 7-membered rings which includes fused ring systems of 9-11 atoms containing at least one and up to four heteroatoms selected from nitrogen, oxygen, or sulfur. Preferred heterocycles of the present invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, azepanyl, diazepanyl, tetrahydrothienyl S-oxide, tetrahydrothienyl S,S-dioxide and homothiomorpholinyl S-oxide.

Compounds prepared according to the methods of the invention can be provided as pharmaceutical compositions. The pharmaceutical compositions can be manufactured in a manner that is itself known, e.g., by means of a conventional mixing, dissolving, granulating, dragee-making, levigating, emulsifying, encapsulating, entrapping or lyophilizing processes.

Pharmaceutical compositions can be formulated in conventional manner using one or more physiologically acceptable carriers comprising excipients and auxiliaries that facilitate processing of the active compounds into preparations that can be used pharmaceutically. Proper formulation is dependent upon the route of administration chosen.

Non-toxic pharmaceutical salts include salts of acids such as hydrochloric, phosphoric, hydrobromic, sulfuric, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

For injection, the compounds prepared according to the methods of the invention can be formulated in appropriate aqueous solutions, such as physiologically compatible buffers such as Hanks's solution, Ringer's solution, or physiological saline buffer. For transmucosal and transcutaneous administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration. For buccal administration, the compositions can take the form of tablets or lozenges formulated in conventional manner.

For administration by inhalation, the compounds prepared according to the methods of the invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

Pharmaceutical formulations for parenteral administration include aqueous solutions of the active compounds in water-soluble form. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances that increase the viscosity of the suspension, such as sodium carboxymethyl cellulose, sorbitol, or dextran. Optionally, the suspension can also contain suitable stabilizers or agents that increase the solubility of the compounds to allow for the preparation of highly concentrated solutions. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for hydrophobic compounds of formula I is a cosolvent system comprising benzyl alcohol, a nonpolar surfactant, a water-miscible organic polymer, and an aqueous phase. The cosolvent system can be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of polysorbate 80; the fraction size of polyethylene glycol can be varied; other biocompatible polymers can replace polyethylene glycol, e.g. polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity. Additionally, the compounds can be delivered using a sustained-release system, such as semipermeable matrices of solid hydrophobic polymers containing the therapeutic agent. Various sustained-release materials have been established and are well known by those skilled in the art. Sustained-release capsules can, depending on their chemical nature, release the compounds for a few weeks up to over 100 days. Depending on the chemical nature and the biological stability of the therapeutic reagent, additional strategies for protein and nucleic acid stabilization can be employed.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The compounds of Formula I can be provided as salts with pharmaceutically compatible counterions. Pharmaceutically compatible salts can be formed with many acids, including but not limited to hydrochloric, sulfuric, acetic, lactic, tartaric, malic, succinic, phosphoric, hydrobromic, sulfinic, formic, toluenesulfonic, methanesulfonic, nitic, benzoic, citric, tartaric, maleic, hydroiodic, alkanoic such as acetic, $HOOC-(CH_2)_n-CH_3$ where n is 0-4, and the like. Salts tend to be more soluble in aqueous or other protonic solvents that are the corresponding free base forms. Non-toxic pharmaceutical base addition salts include salts of bases such as sodium, potassium, calcium, ammonium, and the like. Those skilled in the art will recognize a wide variety of non-toxic pharmaceutically acceptable addition salts.

Pharmaceutical compositions of the compounds prepared according to the methods of the invention can be formulated and administered through a variety of means, including systemic, localized, or topical administration. Techniques for formulation and administration can be found in "Remington's Pharmaceutical Sciences," Mack Publishing Co., Easton, Pa. The mode of administration can be selected to maximize delivery to a desired target site in the body. Suitable routes of administration can, for example, include oral, rectal, transmucosal, transcutaneous, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one can administer the compound in a local rather than systemic manner, for example, via injection of the compound directly into a specific tissue, often in a depot or sustained release formulation.

Pharmaceutical compositions suitable for use include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For administration to non-human animals, the drug or a pharmaceutical composition containing the drug may also be added to the animal feed or drinking water. It will be convenient to formulate animal feed and drinking water products with a predetermined dose of the drug so that the animal takes in an appropriate quantity of the drug along with its diet. It will also be convenient to add a premix containing the drug to the feed or drinking water approximately immediately prior to consumption by the animal.

Preferred compounds prepared according to the methods of the invention will have certain pharmacological properties. Such properties include, but are not limited to oral bioavailability, low toxicity, low serum protein binding and desirable in vitro and in vivo half-lives. Assays may be used to predict these desirable pharmacological properties. Assays used to predict bioavailability include transport across human intestinal cell monolayers, including Caco-2 cell monolayers. Serum protein binding may be predicted from albumin binding assays. Such assays are described in a review by Oravcová et al. (1996, J Chromat. B 677: 1-27). Compound half-life is inversely proportional to the frequency of dosage of a compound. In vitro half-lives of compounds may be predicted from assays of microsomal half-life as described by Kuhnz and Gieschen (1998, DRUG METABOLISM AND DISPOSITION, vol. 26, pp. 1120-1127).

Toxicity and therapeutic efficacy of such compounds can be determined by conventional pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds that exhibit high therapeutic indices are preferred. The data obtained from these cell culture assays and animal studies can be used in formulating a range of dosage for use in humans. The dosage of such compounds lies preferably within a range of circulating concentrations that include the ED50 with little or no toxicity. The dosage can vary within this range depending upon the dosage form employed and the route of administration utilized. The exact formulation, route of administration and dosage can be chosen by the individual physician in view of the patient's condition. (See, e.g. Fingl et al., 1975, in THE PHARMACOLOGICAL BASIS OF THERAPEUTICS, Ch. 1, p. 1).

Dosage amount and interval can be adjusted individually to provide plasma levels of the active moiety that are sufficient to maintain bacterial cell growth-inhibitory effects. Usual patient dosages for systemic administration range from 100-2000 mg/day. Stated in terms of patient body surface areas, usual dosages range from 50-910 mg/m$^2$/day. Usual average plasma levels should be maintained within 0.1-1000:M. In cases of local administration or selective uptake, the effective local concentration of the compound cannot be related to plasma concentration.

The disclosures in this application of all articles and references, including patents, are incorporated herein by reference.

The following Examples are provided for the purposes of illustration and are not intended to limit the scope of the present invention. The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

EXAMPLES

Example 1

General Procedure for the Synthesis of Methyl Diarylborinates

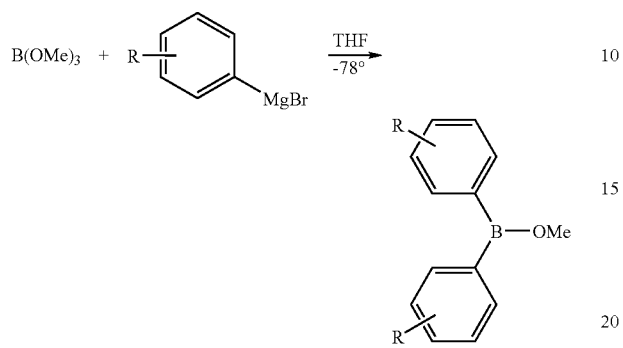

Trimethylborate (0.95 eq) is added dropwise to a freshly prepared solution of aryl magnesium bromide (2 eq) in tetrahydrofuran (0.3 M) under argon at −78° C. The mixture is warmed to room temperature and stirred overnight. The solution is cooled to −78° C. and excess Grignard reagent is destroyed by the dropwise addition of methanol until no more effervescence is observed. Solvents are removed in vacuo and the residue dissolved in diethyl ether followed by a water wash. The organic layer is dried (over $MgSO_4$), filtered and the solvents removed in vacuo to give the product as a foam that can be used without further purification. Any trialkylborate may be used as a substitute for trimethylborate including triethylborate and tributylborate, as discussed above.

Example 2

General Procedure for the Synthesis of N—O Complexed Diarylboronic Acids

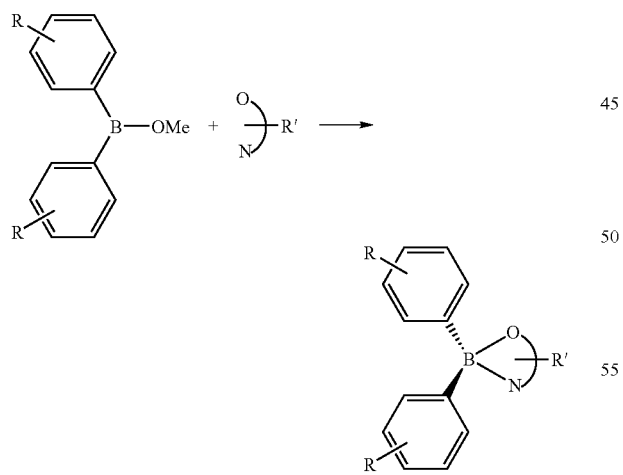

The complexing agent (0.9 eq) is dissolved in methanol (or dichloromethane depending on solubility) and added to a solution of methyl diarylborinate (1 eq) (prepared as outlined above) in methanol. The solution is allowed to stand overnight, if the product has crystallized, the solid is collected and washed with cold ethanol; otherwise the solvents are removed in vacuo to give a solid which is purified by recrystallization from ethanol or diethyl ether (depending on the complexing agent). If this is unsuccessful the product is purified by column chromatography on silica gel eluting with diethyl ether/hexane.

Example 3

Synthesis of methyl di(p-chlorophenyl)borinate

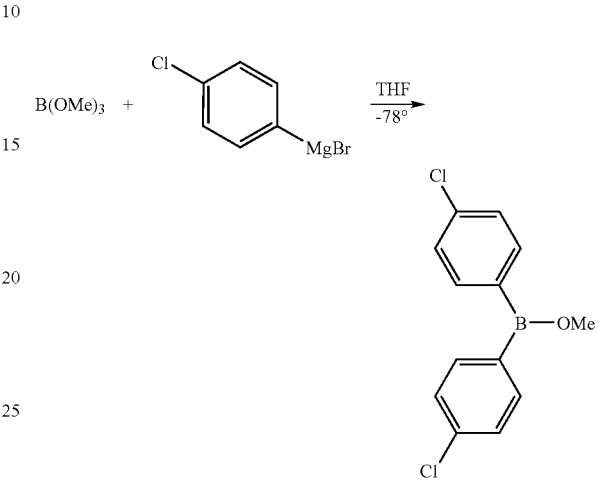

Trimethylborate (2.2 ml, $1.92 \times 10^{-2}$ mol) is added dropwise to a freshly prepared solution of p-chlorophenyl magnesium bromide (40.4 ml, 1 M, $4.04 \times 10^{-2}$ mol) in tetrahydrofuran (60 ml) under argon at −78° C. The mixture is warmed to room temperature and stirred overnight. The solution is cooled to −78° C. and excess grignard reagent is destroyed by the dropwise addition of methanol until no more effervescence is observed. The solvents are removed in vacuo and the residue dissolved in diethyl ether and washed with water. The organic layer is dried ($MgSO_4$), filtered and the solvents removed in vacuo to give methyl di(p-chlorophenyl)borinate (4.60 g, 92%) as a solid which was used without further purification.

Example 4

Synthesis of methyl di(p-fluorophenyl)borinate

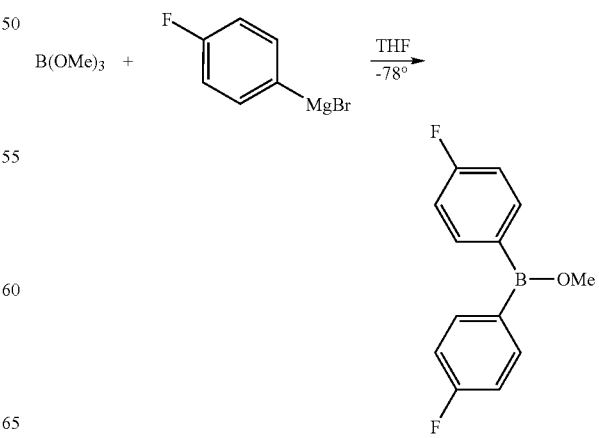

Trimethylborate (1.0 ml, 8.75×10⁻³ mol) is added dropwise to a freshly prepared solution of p-fluorophenyl magnesium bromide (18.4 ml, 1 M, 1.84×10⁻² mol) in tetrahydrofuran (30 ml) under argon at −78° C. The mixture is warmed to room temperature and stirred overnight. The solution is cooled to −78° C. and excess grignard reagent is destroyed by the dropwise addition of methanol until no more effervescence is observed. The solvents are removed in vacuo and the residue dissolved in diethyl ether and washed with water. The organic layer is dried (MgSO$_4$), filtered and the solvents removed in vacuo to give methyl di(p-fluorophenyl)borinate (1.93 g, 89%) as a solid which was used without further purification.

Example 5

Synthesis of methyl di(m-chlorophenyl)borinate

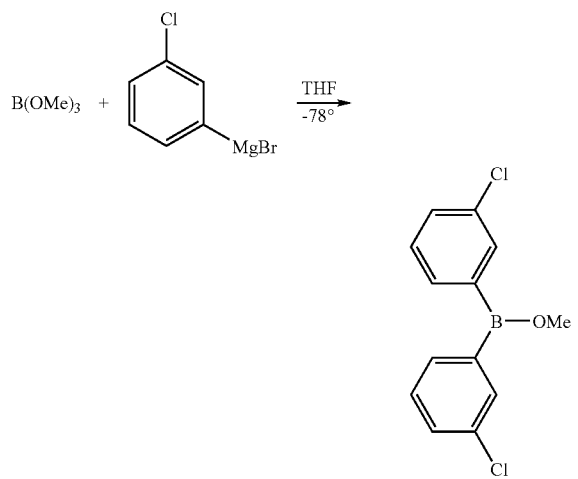

Trimethylborate (1.3 ml, 1.14×10⁻² mol) is added dropwise to a freshly prepared solution of m-chlorophenyl magnesium bromide (48 ml, 0.5 M, 2.39×10⁻² mol) in tetrahydrofuran (30 ml) under argon at −78° C. The mixture is warmed to room temperature and stirred overnight. The solution is cooled to −78° C. and excess grignard reagent is destroyed by the dropwise addition of methanol until no more effervescence is observed. The solvents are removed in vacuo and the residue dissolved in diethyl ether and washed with water. The organic layer is dried (MgSO$_4$), filtered and the solvents removed in vacuo to give di(m-chlorophenyl)borinate (3.2 g, 94%) as a solid which was used without further purification.

Example 6

Di-(p-chlorophenyl)borinic acid 5-nitro-8-hydroxyquinoline ester

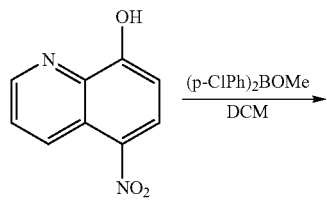

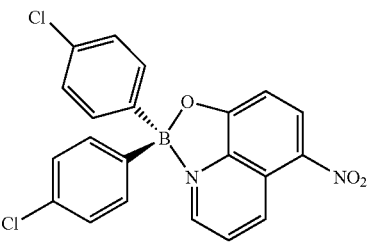

5-Nitro-8-hydroxyquinoline (340 mg, 1.79×10⁻³) was added to a solution of methyl di(p-chlorophenyl)borinate (500 mg, 1.89×10⁻³) in dichloromethane. The solution turned dark yellow and was left to stir overnight. The solvent was removed in vacuo to give a solid, which was washed with diethyl ether (20 ml) and recrystalized from ethanol to give the title compound (630 mg, 83%) as a dark yellow solid.

Example 7

Di-(m-chlorophenyl)borinic acid 8-hydroxyquinoline ester

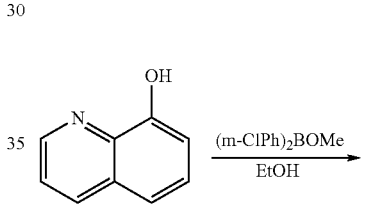

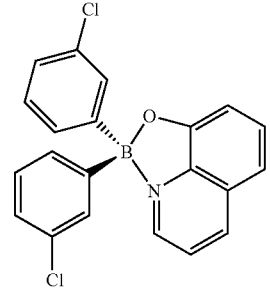

A solution of 8-hydroxyquinoline (2.03 g, 1.4×10⁻² mol) in ethanol (40 ml) was added dropwise to methyl di(m-chlorophenyl)borinate (3.7 g, 1.4×10⁻² mol) in ethanol (40 ml) at room temperature. A yellow precipitation was observed and was left to stand overnight. The solid was collected by filtration and washed with cold ethanol to yield the title product as a yellow solid; mp 144-145° C.; $^1$H-NMR (360 MHz, $C^2H_3^2H$): δ 8.83 (d, J=5.0 Hz, 1H), 8.63 (d, J=8.2 Hz, 1H), 7.78 (dd, J=8.6, 5.0 Hz, 1H), 7.67 (t, J=8.2, 1H), 7.36 (d, J=8.2, 1H), 7.26-7.09 (m, 9H); MS (+ve ESI) m/z 377 ([M+H]$^+$, $^{10}$B, $^{35}$Cl, $^{35}$Cl), 378 ([M+H]$^+$, $^{11}$B, $^{35}$Cl, $^{35}$Cl). 379 ([M+H]$^+$, $^{10}$B, $^{35}$Cl, $^{35}$Cl), 380 ([M+H]$^+$, $^{11}$B, $^{35}$Cl, $^{37}$Cl), 381 ([M+H]$^+$, $^{10}$B, $^{37}$Cl, $^{37}$Cl), 382 ([M+H]$^+$, $^{11}$B, $^{37}$Cl, $^{37}$Cl); Anal. ($C_{21}H_{14}NOBCl_2$) C, H, N.

Example 8

Di-(p-chlorophenyl)borinic acid glycine ester

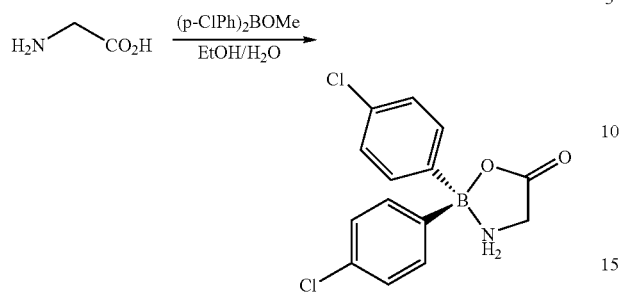

A solution of glycine (67 mg, 8.99×10$^{-4}$ mol) in water (5 ml) was added dropwise to a solution of methyl di(p-chlorophenyl)borinate (250 mg, 9.47×10$^{-4}$ mol) in ethanol (5 ml). The mixture was left to stir overnight. The solvents were removed in vacuo to give a solid, which was washed with diethyl ether (40 ml) and recrystalized from ethanol to give the title compound (225 mg, 82%) as a white solid.

Example 9

Di-(p-chlorophenyl)borinic acid (L)-proline ester

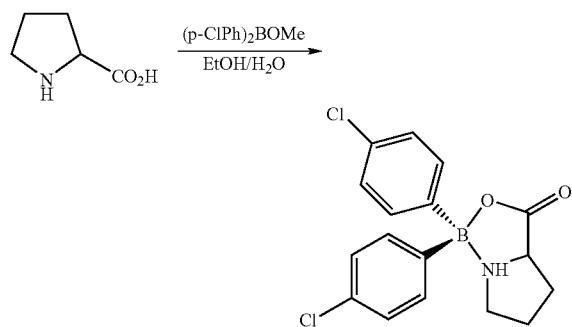

A solution of (L)-proline (54 mg, 4.69×10$^4$ mol) in water (5 ml) was added dropwise to a solution of methyl di(p-chlorophenyl)borinate (130 mg, 4.92×10$^4$ mol) in ethanol (5 ml). The mixture was left to stir overnight. The solvents were removed in vacuo to give a solid, which was washed with diethyl ether (40 ml) and recrystalized from ethanol to give the title compound (149 mg, 90%) as a white solid.

Example 10

Di-(p-chlorophenyl)borinic acid N-hydroxyethyl cytosine ester

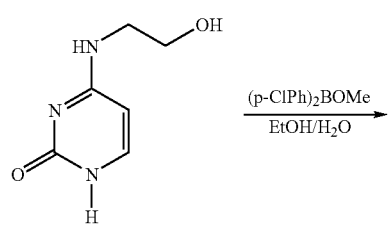

-continued

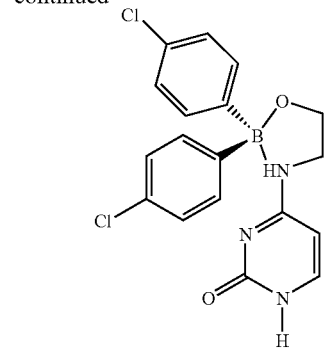

A solution of N-hydroxyethyl cytosine (100 mg, 7.04×10$^{-4}$ mol) in water (5 ml) was added dropwise to a solution of methyl di(p-chlorophenyl)borinate (205 mg, 7.75×10$^{-4}$ mol) in ethanol (5 ml). The mixture was left to stir overnight. The solvents were removed in vacuo to give a solid, which was washed with diethyl ether (30 ml) and recrystalized from ethanol to give the title compound (211 mg, 79%) as a white solid.

Example 11

Di-(p-chlorophenyl)borinic acid N-hydroxyethyl 5-fluorocytosine ester

A solution of N-hydroxyethyl-5-fluorocytosine (364 mg, 2.27×10$^{-3}$ mol) in water (5 ml) was added dropwise to a solution of methyl di(p-chlorophenyl)borinate (659 mg, 2.50×10$^{-3}$ mol) in ethanol (20 ml). The mixture was left to stir overnight. The solvents were removed in vacuo to give a solid, which was washed with diethyl ether (40 ml) and recrystalized from ethanol to give the title compound (773 mg, 86%) as a white solid.

The following compounds are prepared according to the methods of the invention:

| Example No. | Compound |
|---|---|
| 12 | 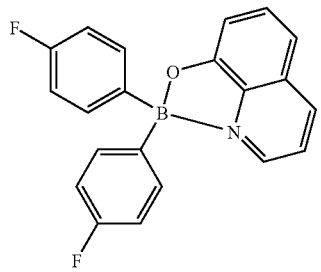<br>di-(p-fluorophenyl)borinic acid 8-hydroxyquinoline ester |
| 13 | 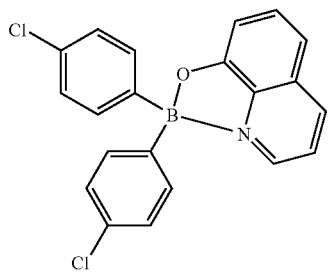<br>di-(p-chlorophenyl)borinic acid 8-hydroxyquinoline ester |
| 14 | 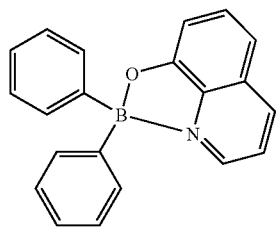<br>diphenylborinic acid 8-hydroxyquinoline ester |
| 15 | 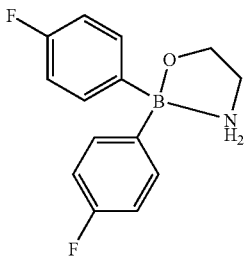<br>di-(p-fluorophenyl)borinic acid ethanolamine ester |
| 16 | 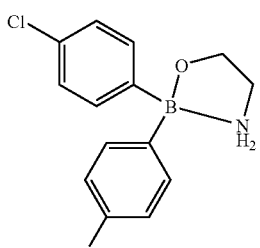<br>di-(p-chlorophenyl)borinic acid ethanolamine ester |

| Example No. | Compound |
|---|---|
| 17 | 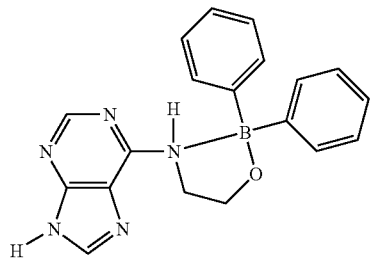<br>6-N-(diphenylborinic ester)-ethyl-adenine |
| 18 | 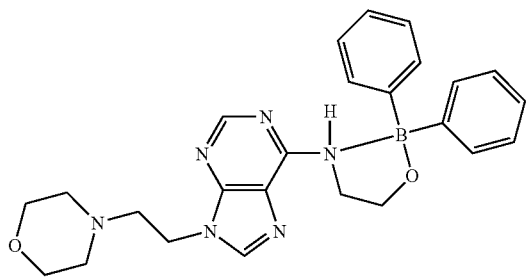<br>6-N-(diphenylborinic ester)-ethyl-9-(2-(4-morpholinyl)-ethyl)-adenine |
| 19 | 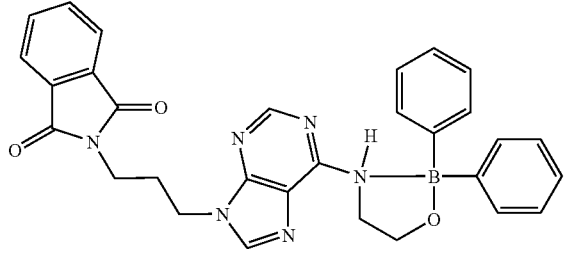<br>6-N-(diphenylborinic ester)-ethyl-9-(3-(N-phthaloyl)-aminopropyl)-adenine |
| 20 | 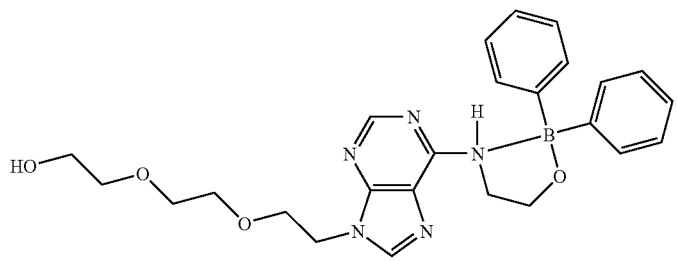<br>6-N-(diphenylborinic ester)-ethyl-9-(2-(2-(2-hydroxyethoxy)ethoxy)-ethyl)-adenine |
| 21 | 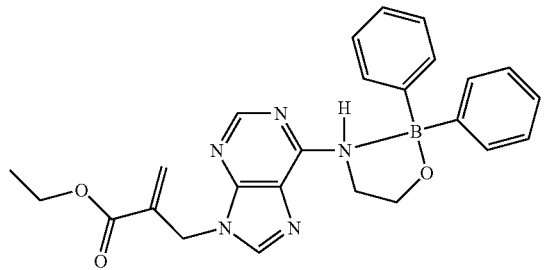<br>6-N-(diphenylborinic ester)-ethyl-9-(ethyl-2-acrylate)-methyl-adenine |

-continued
| Example No. | Compound |
|---|---|
| 22 | 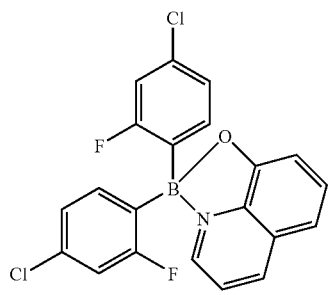  Di-(4-chloro-2-fluorophenyl)borinic acid 8-hydroxyquinoline ester |
| 23 | 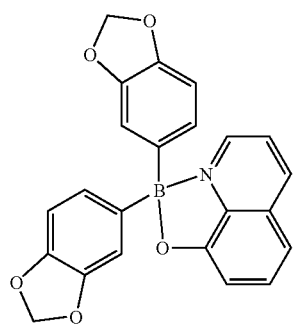  Di-(3,4-methylenedioxyphenyl)borinic acid 8-hydroxyquinoline ester |
| 24 | 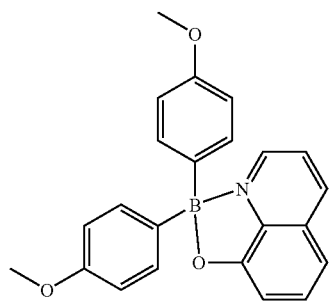  Di-(4-methoxyphenyl)borinic acid 8-hydroxyquinoline ester |
| 25 | 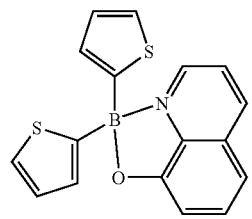  Di-(2-thienyl)borinic acid 8-hydroxyquinoline ester |

-continued
| Example No. | Compound |
|---|---|
| 26 | 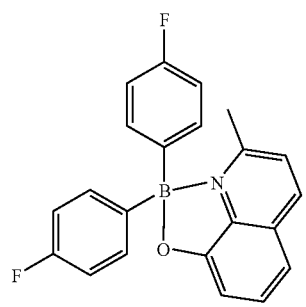<br>Di-(p-fluorophenyl)borinic acid 8-hydroxyquinaldine ester |
| 27 | 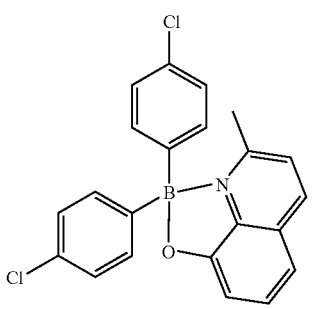<br>Di-(p-chlorophenyl)borinic acid 8-hydroxyquinaldine ester |
| 28 | 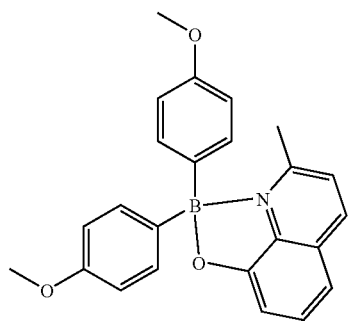<br>Di-(4-methoxyphenyl)borinic acid 8-hydroxyquinaldine ester |
| 29 | 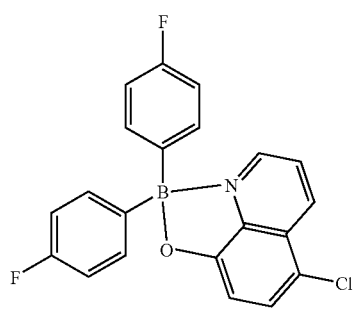<br>Di-(p-fluorophenyl)borinic acid 5-chloro-8-hydroxyquinoline ester |

-continued
| Example No. | Compound |
|---|---|
| 30 | 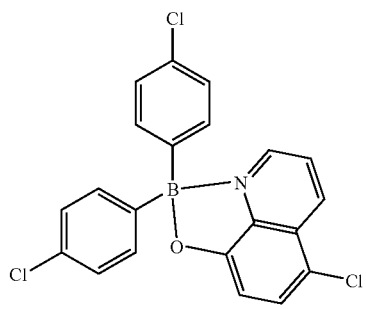<br>Di-(p-chlorophenyl)borinic acid 5-chloro-8-hydroxyquinoline ester |
| 31 | 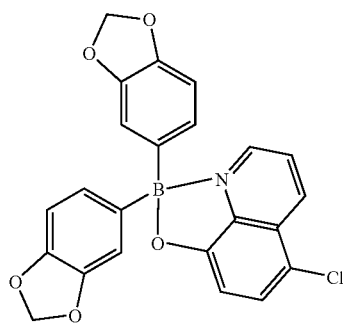<br>Di-(3,4-methylenedioxyphenyl)borinic acid 5-chloro-8-hydroxyquinoline ester |
| 32 | 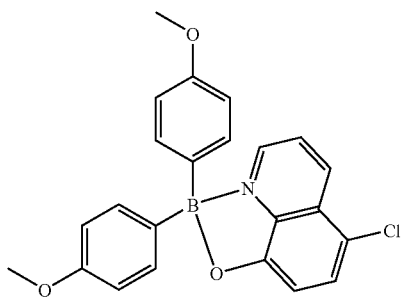<br>Di-(4-methoxyphenyl)borinic acid 5-chloro-8-hydroxyquinoline ester |
| 33 | 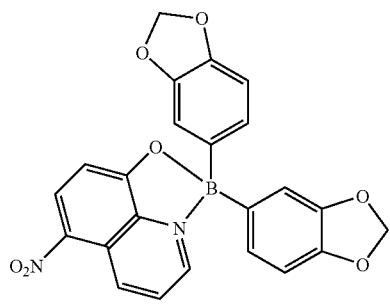<br>Di-(3,4-methylenedioxyphenyl)borinic acid 8-hydroxy-5-nitroquinoline ester |

-continued
| Example No. | Compound |
|---|---|
| 34 | 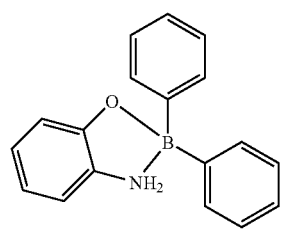<br>Diphenylborinic acid 2-aminophenol |
| 35 | 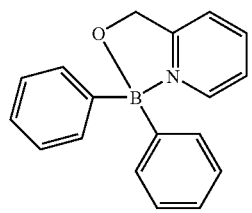<br>Diphenylborinic acid pyridine-2-methanol |
| 36 | 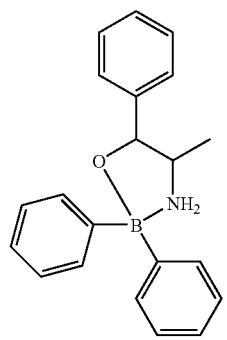<br>Diphenylborinic acid 2-amino-1-phenylpropanol |
| 37 | 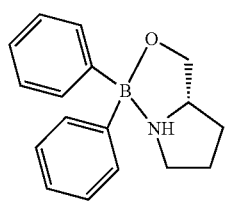<br>Diphenylborinic acid (S)-(+)-pyrrolidine-2-methanol |

-continued
| Example No. | Compound |
|---|---|
| 38 | 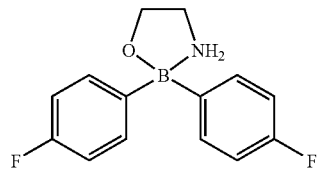<br>Di-(4-fluorophenyl)borinic acid ethanolamine ester |
| 39 | 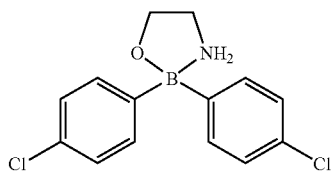<br>Di-(4-chlorophenyl)borinic acid ethanolamine ester |
| 40 | 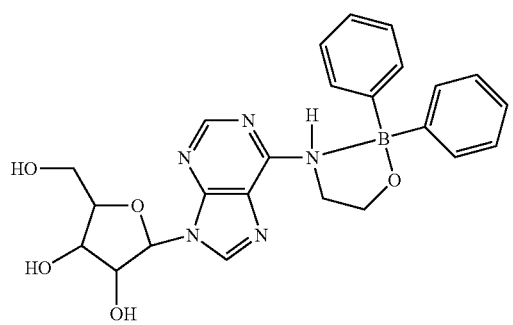<br>6-N-(diphenylborinic ester)-ethyl-9-(2-hydroxymethyl-5-methyl-tetrahydro-furan-3,4-diol)-adenine |
| 41 | 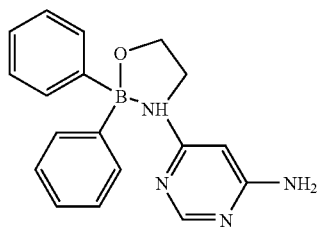<br>6-amino-4(2-diphenylborinic ester) ethylamino pyrimidine |
| 42 | 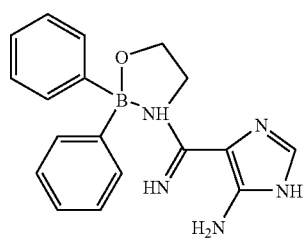<br>4-amino-5(2-diphenylborinic ester ethyliminoester)imidazole. |

What is claimed is:

1. A method for preparing a compound of formula I:

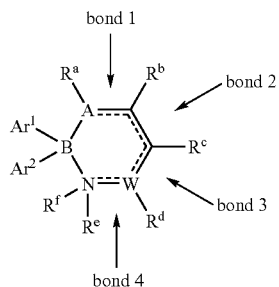

wherein A is O;
W is $C_p$, where p is 0;
$R^b$ and $R^c$ are connected by a phenyl ring optionally substituted with halogen, lower alkyl or lower alkoxy, aryl or substituted aryl, halogen, nitro, nitroso, aldehyde, carboxylic acid, amide, ester, or sulfate, and
$R^c$ and $R^e$ are connected by a phenyl ring optionally substituted with halogen, lower alkyl or lower alkoxy, aryl or substituted aryl, halogen, nitro, nitroso, aldehyde, carboxylic acid, amide, ester, or sulfate, where $R^a$ is absent when A is O, and $R^d$ is absent when p=0;
$R^f$ is hydrogen or is absent; and
wherein $Ar^1$ and $Ar^2$ are independently thienyl or aryl, wherein aryl is optionally substituted at one or a plurality of positions with halogen, nitro, nitroso, lower alkyl, optionally substituted aryl, lower alkoxy, lower alkoxyalkyl, cycloalkyl, or cycloalkyl alkoxy, where each cycloalkyl group has from 3-7 members, and where any member of the aryl or cycloalkyl group is optionally substituted with halogen, lower alkyl or lower alkoxy, aryl or substituted aryl, halogen, nitro, nitroso, aldehyde, carboxylic acid, amide, ester, or sulfate, and
wherein bond 1, bond 2, bond 3 and bond 4 are independently a single bond or a double bond, provided that when A is O, bond 1 is a single bond, said method comprising the step of:
reacting an methyl diarylborinate of formula III with a compound of formula II to form the compound of formula I

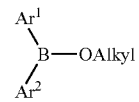

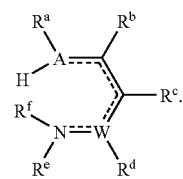

wherein the methyl diarylborinate of formula III and the compound of formula II are in a ratio of about 1 to about 0.9 equivalents respectively; and
wherein the methyl diarylborinate of formula III is prepared by reacting about 1 equivalent of trimethylborate with about 2 equivalents of metalloorganic reagent.

2. The method of claim 1 wherein the compound of formula II is:

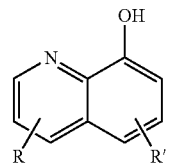

wherein,
R and R' are the same or different and are independently hydrogen, halogen, lower alkyl or lower alkoxy, aryl or substituted aryl, halogen, nitro, nitroso, aldehyde, carboxylic acid, amide, ester, or sulfate.

3. The method of claim 1 wherein the metalloorganic reagent is a Grignard reagent or a lithium reagent.

4. The method of claim 1 further comprising the step of treating the reaction product with methanol.

* * * * *

UNITED STATES PATENT AND TRADEMARK OFFICE
CERTIFICATE OF CORRECTION

PATENT NO.       : 7,405,304 B2
APPLICATION NO.  : 10/501755
DATED            : July 29, 2008
INVENTOR(S)      : Ali Tavassoli and Stephen J. Benkovic It is certified that error appears in the above-identified patent and that said Letters Patent is hereby corrected as shown below:

At column 34, line 10, please delete formula (III) and replace it with the following:

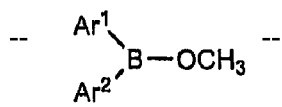

Signed and Sealed this

Eighteenth Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,405,304 B2
APPLICATION NO. : 10/501755
DATED : July 29, 2008
INVENTOR(S) : Tavassoli et al.

It is certified that error appears in the above-identified patent and that said Letters Patent is hereby corrected as shown below:

In Column 1, at line 12, please add
-- STATEMENT REGARDING FEDERALLY SPONSORED RESEARCH OR DEVELOPMENT
This invention was made with government support under Grant No. MDA972-97-1-0008, awarded by DARPA. The Government has certain rights in this invention. --

Signed and Sealed this

Thirty-first Day of March, 2009

JOHN DOLL
*Acting Director of the United States Patent and Trademark Office*